US00PP22515P2

(12) United States Plant Patent
Bunker

(10) Patent No.: US PP22,515 P2
(45) Date of Patent: Feb. 21, 2012

(54) ***EUPHORBIA* PLANT NAMED 'SYEP231'**

(50) Latin Name: ***Euphorbia hypericifolia* (syn. *Chamaesyce hypericifolia*)**
Varietal Denomination: SYEP231

(75) Inventor: Kerry Veianne Bunker, Redland Bay (AU)

(73) Assignee: Syngenta Crop Protection AG, Basel (CH)

( * ) Notice: Subject to any disclaimer, the term of this patent is extended or adjusted under 35 U.S.C. 154(b) by 2 days.

(21) Appl. No.: 12/924,448

(22) Filed: Sep. 28, 2010

(51) Int. Cl.
*A01H 5/00* (2006.01)

(52) U.S. Cl. ..... Plt./302

(58) Field of Classification Search ..... Plt./302
See application file for complete search history.

*Primary Examiner* — Susan McCormick Ewoldt

(74) *Attorney, Agent, or Firm* — S. Matthew Edwards

(57) ABSTRACT

A new *Euphorbia* plant named 'SYEP231' particularly distinguished by the compact and mounded sub-shrub habit with excellent branching, medium green foliage; is highly floriferous and has large white colored flower bracts.

2 Drawing Sheets

Latin name of the genus and species of the plant claimed: *Euphorbia hypericifolia* (syn. *Chamaesyce hypericifolia*).

Varietal denomination: 'SYEP231'.

BACKGROUND OF THE NEW PLANT

The present invention comprises a new *Euphorbia,* botanically known as *Euphorbia hypericifolia* (syn. *Chamaesyce hypericifolia*), and hereinafter referred to by the variety name 'SYEP231'.

'SYEP231' is a product of a planned breeding program. The new cultivar has compact and mounded sub-shrub habit with excellent branching, medium green foliage, is highly floriferous and has large white colored flower bracts.

'SYEP231' originated from a hybridization made in October 2007 in a controlled breeding environment in Queensland, Australia. The female parent was the unpatented proprietary plant designated '07-001' with white flowers, fewer branches and less vigor.

The male parent of 'SYEP231' was a commercially available variety known as 'Inneuphdia', U.S. Plant Pat. No. 17,567, with white flowers, lighter green foliage, and fewer flowers. The seed was sown in January 2008.

'SYEP231' was selected as one flowering plant within the progeny of the stated cross in the September 2008 in a controlled environment in Queensland, Australia.

The first act of asexual reproduction of 'SYEP231' was accomplished when vegetative cuttings were propagated from the initial selection in September 2008 in a controlled environment in Queensland, Australia.

BRIEF SUMMARY OF INVENTION

'SYEP231' has not been observed under all possible environmental conditions. The phenotype may vary significantly with variations in environment such as temperature, light intensity and day length.

A Plant Breeder's Right for this cultivar was applied for in Canada on Apr. 28, 2010 (#10-6945). 'SYEP231' has not been made publicly available more than one year prior to the filing of this application.

The following traits have been repeatedly observed and are determined to be basic characteristics of the new variety. The combination of these characteristics distinguishes this *Euphorbia* as a new and distinct variety.

BRIEF DESCRIPTION OF THE PHOTOGRAPHS

The accompanying photographic drawings show typical flower and foliage characteristics of 'SYEP231' with colors being as true as possible with an illustration of this type.

Figure 1:
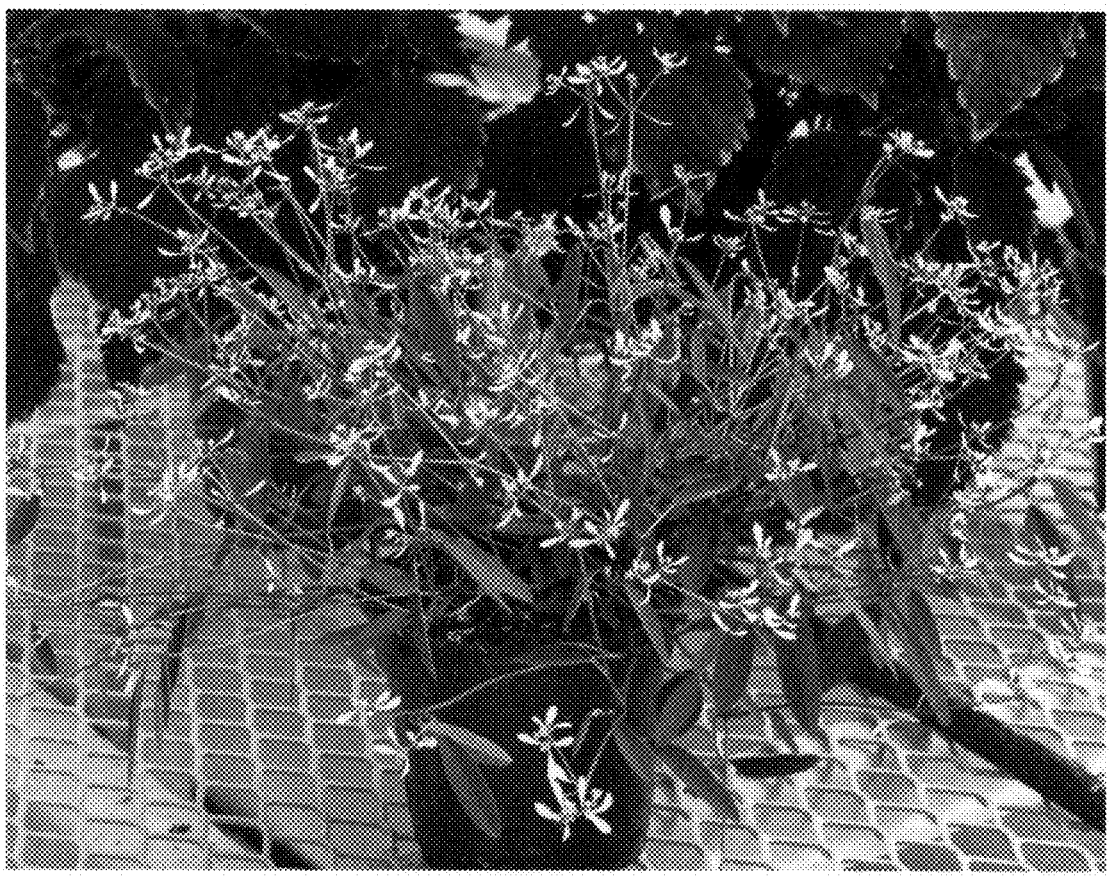
Figure 2:
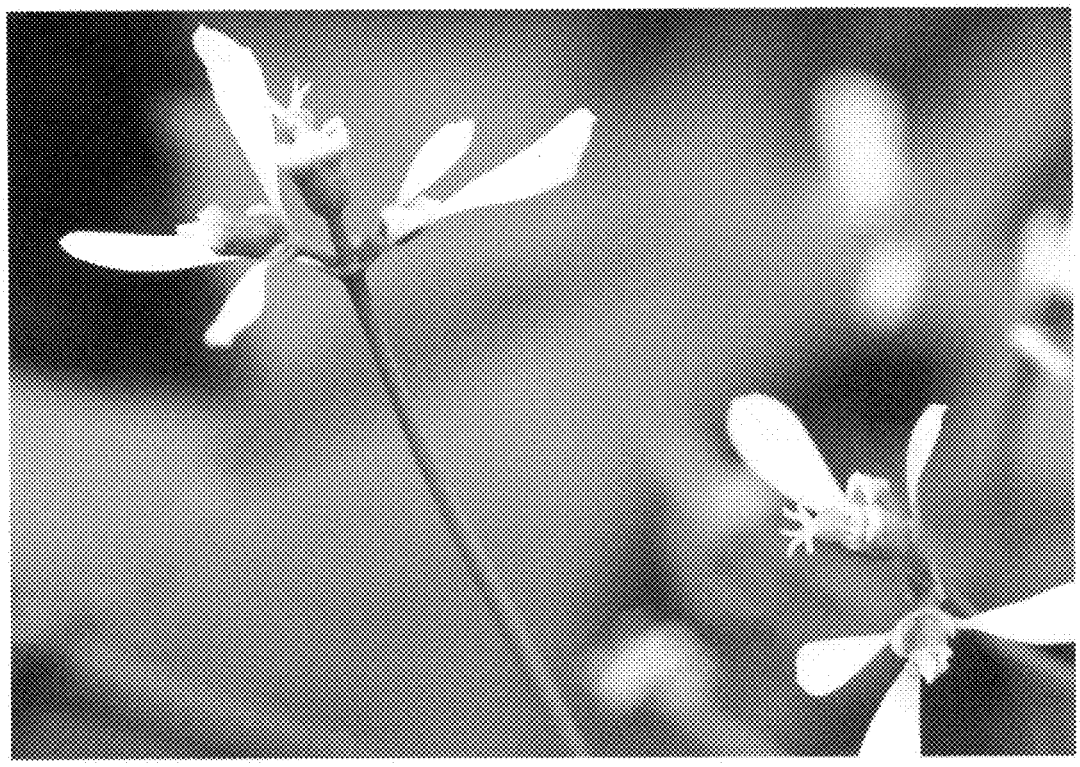
Figure 3:
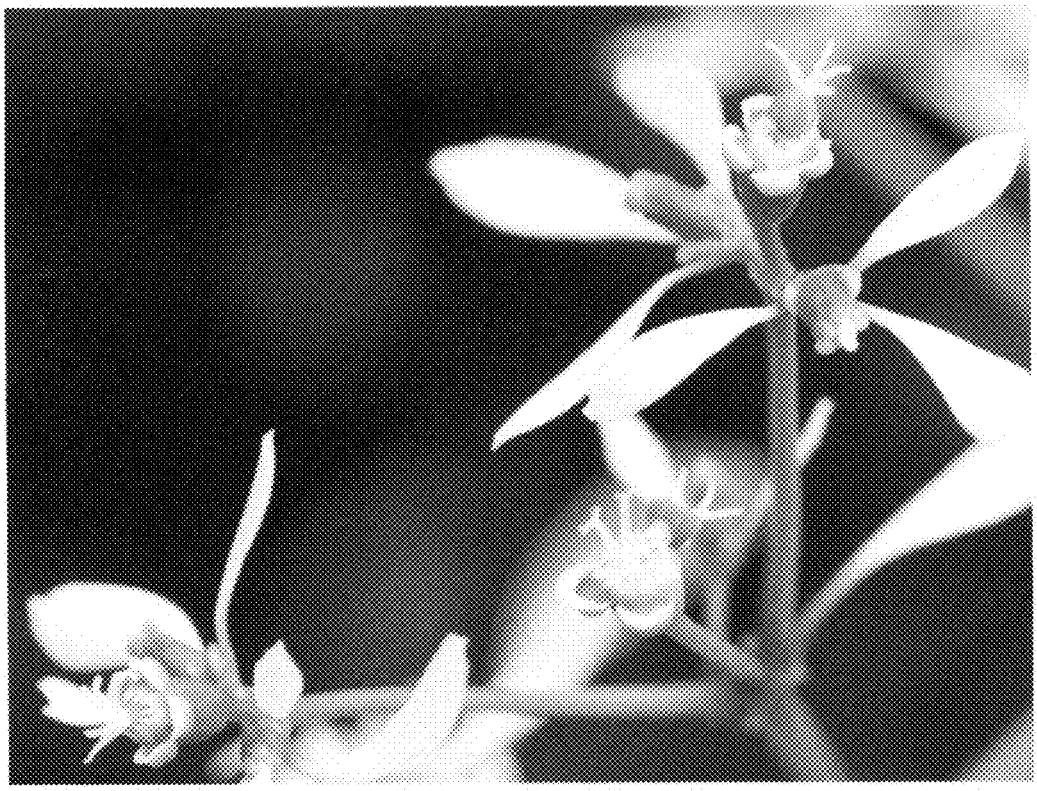

The photographic drawing shows in FIG. 1. a flowering potted plant of the new variety, in FIG. 2 and in FIG. 3 close-ups of the inflorescence.

DETAILED BOTANICAL DESCRIPTION

The plant descriptions, measurements and aforementioned photographs were taken in late April 2010 in Gilroy, Calif. on 14-16 week old plants that had been planted into 4 inch pots.

Color references are made to The Royal Horticultural Society Colour Chart (R.H.S.) 2001.

TABLE 1

DIFFERENCES BETWEEN THE NEW VARIETY 'SYEP231' AND A SIMILAR VARIETY

| | 'SYEP231' | 'Inneuphdia' (U.S. Plant Pat. No. 17,567) |
|---|---|---|
| Foliage color: | RHS 137A | RHS 147A |
| Flower quantity: | More | Less |
| Inflorescence arrangement: | Held more above the foliage | Held closer to the plant |
| Plant habit: | Fuller plant with more branching | Less full plant with fewer branches |

Plant:

*Form, growth and habit.*—Very low compact and mounded sub-shrub, upright and outwardly spreading, excellent branching and vigor.

*Plant height* (*excluding inflorescences*).—About 10.0 cm.

*Plant height* (*inflorescence included*).—About 20.0 cm.
*Plant width.*—30-46 cm.

Roots:
*Number of days to initiate and produce roots.*—Approximately 18-30 days at about 22 degrees C.
*Type.*—Fine, fibrous, free branching.
*Color.*—RHS N155B but whiter.

Foliage:
*Arrangement.*—Alternate.
*Immature, leaf color, upper surface.*—RHS 144A but a little darker.
*Lower surface.*—Closest to RHS 146C.
*Mature, leaf color, upper surface.*—Closest to RHS 137A.
*Lower surface.*—Between RHS 137B and RHS 137C.
*Length.*—3.2-3.7 cm.
*Width.*—1.2-1.7 cm.
*Shape.*—Oblong to elliptical.
*Base shape.*—Attenuate.
*Apex shape.*—Obtuse.
*Margin.*—Entire.
*Texture, upper surface.*—Smooth.
*Lower surface.*—Slightly hirsute mainly on the midvein.
*Venation.*—Pinnate.
*Color of veins, upper surface.*—Indistinct.
*Color of veins, lower surface.*—Indistinct.
*Petiole aspect.*—Horizontally to slightly downward directed, while the leaf blades are slanting downward.
*Petiole color.*—RHS 138B, with sometimes a hint of RHS 166A to RHS 166B.
*Length.*—1.0-1.3 cm.
*Diameter.*—0.75-0.1 cm.
*Texture.*—Smooth; glabrous.

Stem:
*Color of stem.*—RHS 146A ground color; with RHS 183A anthcyanins at the nodes; and close to RHS 197A anthocyanins on the older stems and branches.
*Length of stem.*—8.0-12.0 cm.
*Diameter.*—0.2-0.25 cm.
*Length of internodes.*—3-5 cm.
*Texture.*—Smooth, glabrous.
*Color of peduncle.*—RHS 137C but a brighter green.
*Length of peduncle.*—About 4-5.2 cm.
*Peduncle diameter.*—0.1 cm.
*Texture.*—Smooth; glabrous.

Pedicel:
*Color of pedicel.*—RHS 137C but greener.
*Length of pedicel.*—0.4-1.5 cm.
*Pedicel diameter.*—0.1 cm.
*Texture.*—Smooth; glabrous.

Inflorescence:
*Form of inflorescence.*—Cyme, subtended by involucres (bracts).
*Arrangement.*—Axillar and terminal corymbs.
*Natural flowering season.*—Spring to summer; flowers continuous during this period.
*Duration of flowering.*—Throughout the spring and summer.
*Fragrance.*—None.
*Quantity of inflorescences.*—40-50.
*Diameter of inflorescence.*—About 2.5-4.0 cm for the terminal corymbs.
*Vertical diameter of inflorescence.*—1.8-2.5 cm.
*Number of involucre per inflorescence.*—2.
*Single bract, shape.*—Oblanceolate or spathulate.
*Bract, apex.*—Apiculate.
*Bract, base.*—Acute.
*Bract, length.*—1.0-1.1 cm.
*Bract, width.*—0.2 cm at the widest point.
*Bract color, upper side.*—RHS 155D but whiter.
*Bract color, lower side.*—RHS 155D but whiter.
*Texture.*—Papillose.
*Bract petiole length.*—0.1-0.2 cm.
*Bract petiole diameter.*—0.1 cm.
*Petiole color.*—RHS 143C.

Cyme (true inflorescence):
*Form.*—One or two cyathia bearing staminate flowers on top.
*Cyme, diameter.*—0.5-0.9 cm.
*Cyathium, shape.*—Ovate.
*Cyathium, diameter.*—0.25-0.3 cm.
*Cyathium, length.*—0.3 cm.
*Cyathium, color.*—RHS 143B.
*Nectar cups.*—Usually 5 per cyathium, not all developing quite at the same time.
*Nectur cup, width.*—0.1 cm.
*Nectar cup, color.*—RHS N155B.

Reproductive organs:
*Stamen* (*actually staminate flowers*).—Usually in a small bunch at the top of the cyathium.
*Shape.*—Strap-like.
*Filament color.*—RHS 155D.
*Filament length.*—0.1-0.2 cm.
*Anther color.*—RHS 10C.
*Anther diameter.*—Less than 0.1 cm.
*Pollen quantity.*—Moderate (normal quantity for the species).
*Pollen color.*—RHS 10D.
*Pistils* (*actually female flowers*).—Emerges out of the top of the cyathium, initially held upright on a short stem that lengthens and bends downward with maturity.
*Shape.*—Round ovary with 5-lobed stigma with practically no style.
*Stigma color.*—RHS 155A.
*Ovary color.*—RHS 143B.
*Ovary diameter.*—0.1-0.2 cm.
*Fertility/seed set.*—Not observed.

Disease/pest resistance: Disease/pest resistance has not been observed on this hybrid.

What is claimed is:

1. A new and distinct variety of *Euphorbia* plant named 'SYEP231' substantially as illustrated and described herein.

* * * * *